(12) United States Patent
Koska (10) Patent No.: US 6,368,306 B1
(45) Date of Patent: Apr. 9, 2002

(54) SYRINGES

(76) Inventor: Marc Koska, 201 Rockwood Park, Saint Hill Green, West Sussex, RH19 4JX (GB)

( * ) Notice: Subject to any disclaimer, the term of this patent is extended or adjusted under 35 U.S.C. 154(b) by 0 days.

(21) Appl. No.: 09/214,458

(22) PCT Filed: Jul. 11, 1997

(86) PCT No.: PCT/GB97/01889

§ 371 Date: Jul. 27, 1999

§ 102(e) Date: Jul. 27, 1999

(87) PCT Pub. No.: WO98/02198

PCT Pub. Date: Jan. 22, 1998

(30) Foreign Application Priority Data

Jul. 15, 1996 (GB) .............................................. 9614807
May 9, 1997 (GB) .............................................. 9709315

(51) Int. Cl.[7] .......................................... A61M 5/315
(52) U.S. Cl. ...................................... 604/218; 604/220
(58) Field of Search ................................ 604/218, 220, 604/221, 222, 187, 228, 110

(56) References Cited

U.S. PATENT DOCUMENTS

| 3,478,937 A | 11/1969 | Solowey ..................... 222/386 |
| 3,951,146 A | 4/1976 | Chiquiar-Arias ............. 128/218 |
| 4,252,118 A | 2/1981 | Richard et al. .............. 128/218 |
| 4,367,738 A | 1/1983 | Legendre et al. ............. 128/218 |
| 4,424,817 A | 1/1984 | Williams ..................... 128/766 |
| 5,019,045 A | 5/1991 | Lee ............................. 604/110 |
| 5,106,372 A | 4/1992 | Ranford ....................... 604/110 |
| 5,370,620 A | 12/1994 | Shonfeld ..................... 604/110 |

FOREIGN PATENT DOCUMENTS

| EP | 0 022 977 | 1/1991 | |
| EP | 0409134 A | * 1/1991 | |
| EP | 0 409 134 | 1/1991 | |
| GB | 2 184 657 | 7/1987 | |
| GB | 2 213 068 | 8/1989 | |
| GB | 2 256 146 | 12/1992 | |
| WO | WO 89/04187 | 5/1989 | |
| WO | WO 89/06146 | 7/1989 | |
| WO | WO 90/03818 | 4/1990 | |
| WO | WO 94/13339 | 6/1994 | |
| WO | WO 95/10314 | 4/1995 | ............ A51M/5/10 |

* cited by examiner

*Primary Examiner*—Manuel Mendez
(74) *Attorney, Agent, or Firm*—Michael Best & Friedrich LLC; J. Warren Whitesel (57) ABSTRACT

A syringe comprises a barrel (1) having a plunger (7) in slidable and sealing engagement therewith. In order to provide an autodestruct system, so that the syringe can be used once only, being rendered disabled after one normal use, the barrel (1) has means interrupting the cylindrical surface of its inner wall in the form of grooves (10, 11) or a projection (29), and the plunger (7) has a locking means (17, 20) which operates on engagement with a groove (10, 11) or projection (29) on withdrawal of the plunger (7) to prevent further withdrawal movement. The locking means (17, 20) is provided on the head of the plunger (7) adjacent an elastomeric sealing cap (15). The locking means may comprise a pair of flukes (17) or a cross-shaped disc (20).

27 Claims, 6 Drawing Sheets

SYRINGES

This invention relates to syringes and has for its object an autodestruct syringe, that is, one that can be used once only and is rendered disabled by the user during the process of normal use.

Since the early 1980's the spread of AIDS, Hepatitis and other diseases has partly occurred due to the reusing of syringes. The majority of syringes are of a disposable nature, being easy to manufacture in plastics and are often marked "Use once and destroy". However there is no inbuilt barrier within the product to prevent it from being used more than once and by more than one person.

Drug abusers have certain ritualistic techniques that must be fully accommodated if an autodestruct syringe design is to be successful and accepted in this vital market segment. Drug abusers can require to insert a needle many times before a suitable injection site is found, and make numerous small insertions and withdrawals during this process. After an injection a user may choose to flush out any drug left in the "dead space" of the syringe with their own blood several times.

The primary area of concern with the spread of the previously mentioned diseases is that of the drug abuser, but all areas can benefit from such a syringe, if it in no way hinders the user in the use of it.

Many attempts have been made to provide such an autodestruct syringe and examples of designs are shown in U.S. Pat. No. 3,951,196, U.S. Pat. No. 4,220,157, U.S. Pat. No. 4,252,118, GB-A-2184657, U.S. Pat. No. 3,478,937, U.S. Pat. No. 4,367,738, and EP-A-029017. However, to date no design has reached the market, either because of complexities in manufacture, or increase in costs. Furthermore earlier designs have not been suitable for the variety of techniques employed by users, in particular the drug abusers, and may not feel "normal"in use.

Some previous designs have used projection means within the barrel. These however may disrupt the forward motion of the plunger during the injection, and can be "felt" by the user. This is caused by the interaction with the projection means by an elastomeric cap affixed to the plunger.

Other designs have a breakable means inbuilt to the design so that part of the plunger separates leaving the syringe inoperable. This can be a health risk as it leaves an unprotected piece of broken plastic which has recently been inside a barrel possibly containing contaminated blood. By the removal of part of the plunger the barrel is further exposed to abuse and possible conversion to a working unit. Some previous ideas have only been operable in a syringe with an integrated needle as this protects them from tampering and subsequent reuse.

Therefore the ideal product is one which fits closely in with the current manufacturing techniques and assembly procedures, offers no resistance to the user, and is truly autodestruct so that it cannot be tampered with.

According to the first aspect of the present invention, a syringe comprises a barrel having a plunger in slidable and sealing engagement therein, in which the barrel has at least one means interrupting a cylindrical surface of its inner wall, and the plunger has a locking means, the arrangement being such that the locking means operates on engagement with an interruption means on withdrawal of the plunger to prevent further withdrawal movement.

The arrangement allows for use of the syringe in a normal way but is rendered unfit for further use after one injection by operation of the locking means.

Preferably, an interruption means is arranged adjacent the distal end of the barrel. The distal end is the end to which the needle is attached. It is not possible to withdraw the plunger further than the distal end interruption means once the injection has taken place. The interruption means may be positioned to allow flushing after a full injection, but prevent refilling of the barrel. A further interruption means may be located at the proximal end of the barrel. This prevents removal of the plunger prior to use, which would serve as a total tamper proof feature.

The interruption means is preferably arranged at an angle other than 90° to the longitudinal axis of the barrel. This allows friction between the plunger and the interruption means to be dissipated as only part of the interruption means is in contact with the plunger at any one moment. The interruption means preferably extends round the whole circumference of the barrel.

Each interruption means may be a projection. Quite a small projection enables the locking means to operate, and if arranged at an angle will not disrupt the forward motion of the plunger, so that it is not "felt" by the user.

Preferably however each interruption means comprises a groove. Grooves offer no resistance to the plunger, so that a normal feel to the injection is achieved. They are also more positive in ensuring operation of the locking means.

It would also be possible for the interruption means to comprise a groove followed by a projection.

Angled grooves and projections are much easier to produce by injection moulding than those at right angles to the barrel axis.

Each projection or groove is preferably of substantially triangular cross-section, with a first edge inclined slightly to the cylindrical surface, and a second edge inclined sharply to the cylindrical surface. The first edge allows normal forward movement of the plunger, while the second edge engages the locking means on withdrawal movement. The first edge is preferably at an angle of between 20° and 30° to the cylindrical surface. The second edge is substantially perpendicular to the first edge, and at an angle of between 60° and 70° to the cylindrical surface.

Preferably the head of the plunger has means, such as a peg, with which an elastomeric sealing cap engages, and the locking means is also arranged on the head of the plunger, adjacent the cap. The plunger head locks into the interruption means and jams, effectively rendering the syringe useless. The plunder remains intact, filling the barrel, and acting as an anti-tamper block. If excess effort is applied in the removal it may break at the joint between the stem of the plunger rod and head. However, this is not the object of the design as the locking feature is more than adequate to prevent reuse and the more preferable.

The locking means preferably comprises two rearward facing flukes attached to the head by a flexible connection, movable in each direction but engaging with the interruption means on withdrawal movement away from the distal end of the barrel. When engaging with for example an angled groove the head of the plunger is deflected in the barrel perpendicular to the groove so that both flukes are located in the groove, as far as the flexibility of the connection and the elasticity of the elastomeric cap will permit. Alternatively, the locking means comprises a disc attached to the head, and having a flexible periphery which slides in either direction, but engages with the interruption means on withdrawal movement. It is preferably held by the head in the locked position. The disc may be cross-shaped.

The design can be incorporated into a syringe product with or without an integrated needle. However the present invention benefits from being tamper proof in an open luer type syringe barrel and in a barrel with an integrated needle.

The invention also has the advantage that the syringe is made of two plastics parts manufactured by injection moulding, being the barrel and the plunger. The plunger is made with the peg over which the elastomeric cap is fitted to engage and seal with the inner wall of the barrel.

The plunger is moulded in a traditional mould which can be manufactured to include either of the modifications described. Alternatively a new or existing mould can be fitted with inserts which relate to this fluke/connection or disc area. This means an existing product can be changed to include the modification of this invention for relatively low capital costs. Likewise the barrel described in this invention can be produced through modification of the moulding cores for the barrel, which again is only a fraction of the total capital for such a moulding tool.

Further aspects of the invention relate to apparatus for making a syringe plunger including the locking means.

According to a second aspect of the invention, apparatus for making a syringe plunger adapted to slide in a syringe barrel and having a locking means adapted to engage an interruption means in the inner wall of the barrel comprises a two-part moulding tool, each part bearing an impression of a portion of the plunger such that the two parts co-operate to make the whole plunger, and each part having a removable insert bearing the impression for the locking means for the respective plunger portion.

According to a third aspect of the invention, an insert is adapted to be used in apparatus for making a syringe plunger adapted to slide in a syringe barrel and having a locking means adapted to engage an interruption means in the inner wall of the barrel the apparatus comprising a two-part moulding tool, each part bearing an impression of a portion of the plunger such that the two parts co-operate to make the whole plunger, the insert bearing the impression for the locking means of the respective plunger portion and being adapted to be mounted removably in the corresponding tool part.

The second and third aspects of the invention enable moulding tools for existing plungers to be modified to include the inserts with the locking means. The existing plungers can therefore be readily changed to include the locking means, but with low capital costs, as complete new tools are not required.

Further the inserts can themselves be readily changed. The moulding tool wears with use, but wear to the portion containing the locking means is critical, as it can render the locking means inoperable. The amount of acceptable wear for the locking means is much less than that for the rest of the plunger. The inserts with the locking means can therefore be changed often, to ensure accurate manufacture of the locking means.

The inserts may be located at an existing split line in a tool part. Each insert may be attached to the tool part by pins inserted in aligned openings in the insert and tool part. Alternatively they may be secured by packing.

It is also possible for the tool part to be provided with cavities for receiving the insets. The cavities may be cut or machined in the tool part.

Each insert may comprise one or more plates.

In order that the invention may be more readily understood, embodiments thereof will now be described by way of example, with reference to the accompanying drawings, in which.

Figure 1:
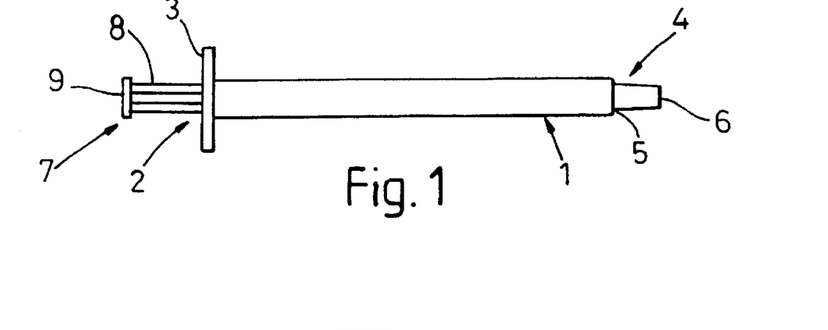
FIG. 1 is a side elevation of a syringe constructed in accordance with one embodiment of the invention.
Figure 2:
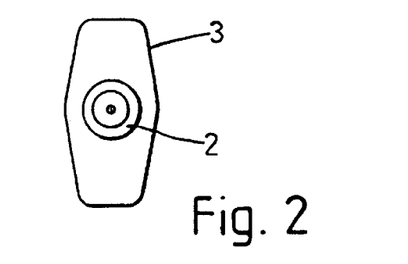
FIG. 2 is an end view of the syringe barrel of the syringe in FIG. 1 looking from the proximal end.
Figure 3:
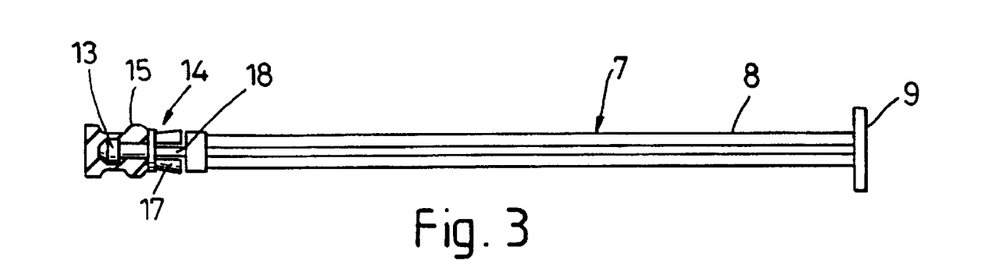
FIG. 3 is a side elevation of the syringe plunger of the syringe in FIG. 1.

Referring to FIGS. 1 and 2 of the drawings the syringe comprises a barrel 1 and a plunger 7. The barrel has an inner cylindrical surface, an open proximal end 2 provided with a gripping flange 3 and a distal end 4 having an internal abutment shoulder 5 encircling a liquid outlet 6. The liquid outlet 6 can be arranged in a variety of ways as needed; the one shown is a luer slip design which holds a needle (not shown) with a friction fit; a luer lock onto which a needle screws; or can be arranged to accept a needle which affixed permanently by glue, heat or some other means. The syringe plunger 7, shown inserted, comprises a rod 8 and finger plate 9, for gripping the plunger. At the distal end of the rod 8 is an elastomeric sealing cap 15, adjacent to which are formed locking means 17 adapted to engage with means interrupting the cylindrical surface of the inner barrel wall, comprising grooves 10, 11, as explained in more detail below, in order to provide an autodestruct construction.

Figure 16:
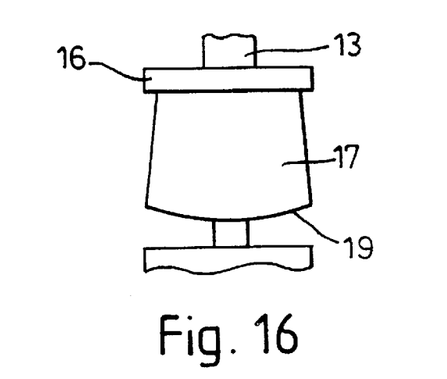
FIG. 16 is an alternative design for the syringe plunger distal end.

As shown in FIGS. 3 to 6, the plunger 7 has the traditional rod 8 and finger plate 9 used for pushing in and pulling out the plunger. At the distal end the plunger has a head 14 comprising a peg 13 over which is fixed an elastomeric cap 15 which forms a complete seal for liquids and gasses in the barrel 1. The peg 13 has a base 16 which supports the cap 15. On the opposite side of the base 16 is a tubular connection 18 to the plunger rod 8 which forms a strong yet slightly flexible join. Also affixed to the base 16 are two flukes 17, which form the locking means. The flukes are arranged so that their outer radial proximal edges 19 are in contact with the inner barrel wall when assembled. The axial edge can be arranged with a straight edge as in FIG. 4 or have an arcuate edge such as shown in FIG. 16. The edge 19 may also have a variety of arrangements to best match the grooves in the barrel.

Figure 4:
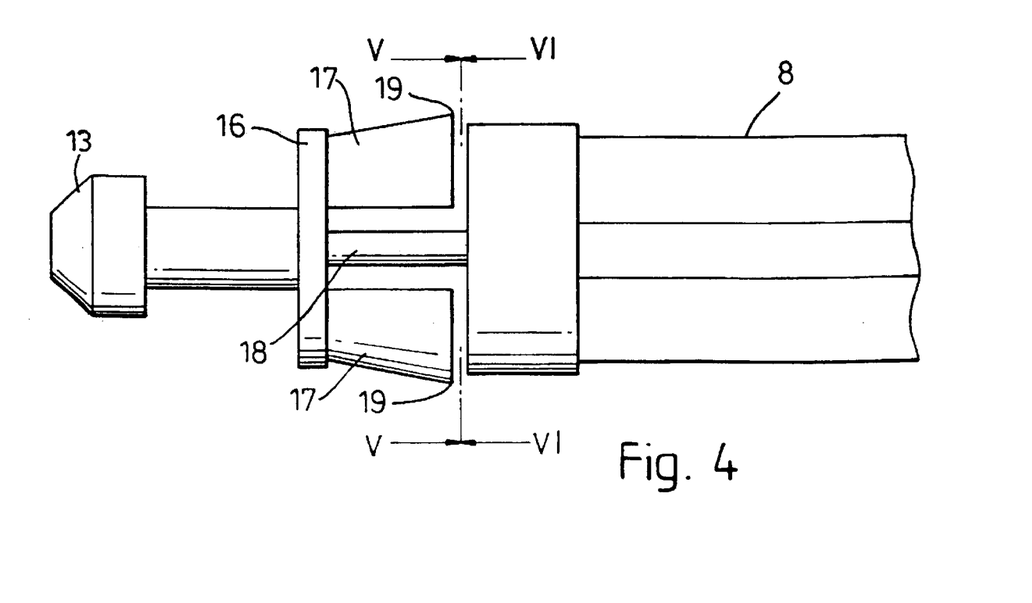
FIG. 4 is an enlarged view of the distal end region of the syringe plunger.
Figure 5:
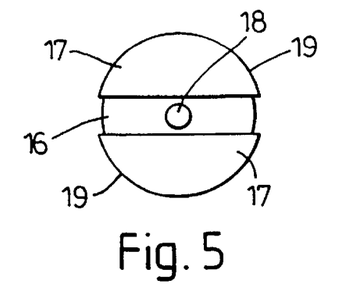
FIG. 5 is a cross-section taken along the line V—V of FIG. 4 and looking in the direction of the arrows.

The flukes 17 project outside the base 16 when viewed in FIG. 5 which is a cross-sectional view as shown by the arrows V—V in FIG. 4. The base does not touch the inner wall of the barrel but this drawing shows the arrangement of how the flukes will project and make contact with the barrel wall.

Figure 6:
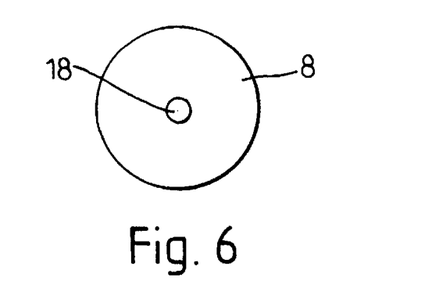
FIG. 6 is a cross-section taken along the line V1—V1 of FIG. 4 and looking in the direction of the arrows.

The position of the connection 18 is shown clearly in FIG. 6.

Figure 7:
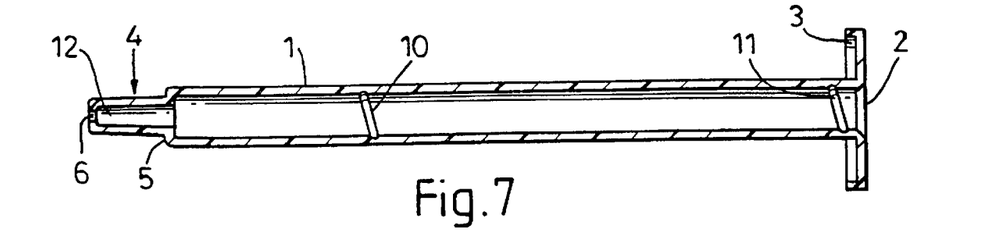
FIG. 7 is a longitudinal section of the syringe barrel of the syringe in FIG. 1.

FIG. 7 is a longitudinal section through the barrel showing the position and typical angle of location of the grooves 10, 11. The distal groove 10 is arranged in a suitable position for the use of the syringe. In this example the groove 10 is in a position to allow for aspiration after the full injection stroke of the plunger. This is vital in some syringe use to allow the user to check the needle is still placed within a blood vessel, and/or to allow a drug abuser to flush the drug from the dead space 12 through drawing in and expelling blood. The proximal groove 11 is positioned to allow a complete rearward motion with the plunger, but does not allow the plunger to be removed. This has two advantages: it can be position to indicate when a certain volume of fill with a liquid has been achieved, which can be useful with sight impaired users. Also, this groove prevents the removal of the plunger from the barrel once it has been assembled. Therefore the plunger cannot be replaced or tampered with to render the syringe reusable.

Figure 8:
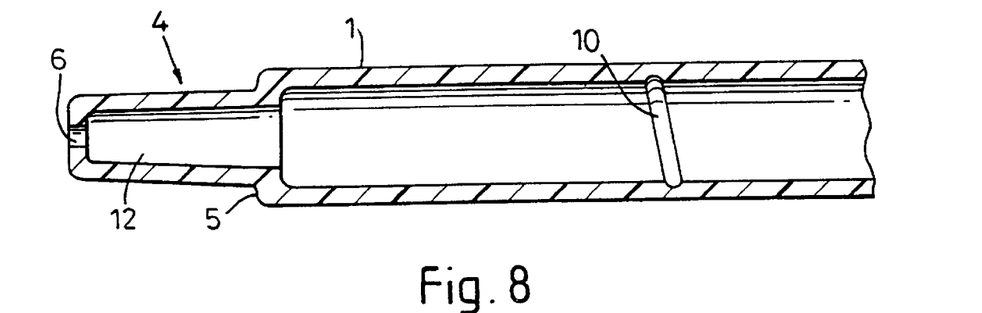
FIG. 8 is a longitudinal section of the distal end region of the syringe barrel, to an enlarged scale.
Figures 9, 15:
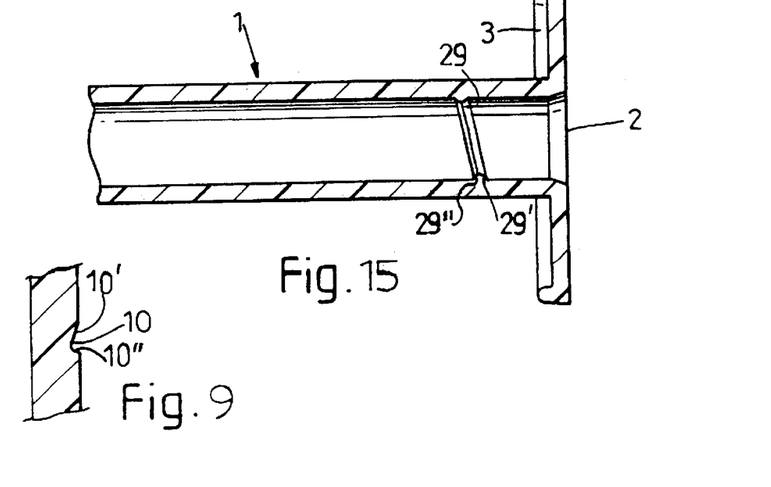
FIG. 9 is a detail view of the groove as shown in FIG. 8.
FIG. 15 is a longitudinal section of the proximal end region of the syringe barrel, to an enlarged scale and showing a modification.

The groove 10 is shown in detail in FIG. 8, and in section in FIG. 9. The groove 10 extends round the whole of the circumference of the inner wall, and is of substantially triangular cross-section. The groove 10 has a first, distal edge 10' which is slightly inclined, by 20° to 30°, to the inner wall to allow forward movement of the plunger. It has a second, proximal edge 10" more sharply inclined, by about 60° to 70° to the inner wall, to engage the locking means 17 on withdrawal. The first and second edges are substantially perpendicular. The groove 10 is also arranged at an angle other than perpendicular to the longitudinal axis of the barrel 1. This angle, which may be up to 30°, means that on advance of the elastomeric cap 15, the friction felt by the user is not the same as the friction experienced when advancing in and past a groove or projection arranged perpendicular to the barrel axis. The cap 15 meets the proximal edge of the groove 10 first. The elastomeric cap 15 has a leading edge which forms a tight seal with the inner wall of the barrel and exerts a slight outward pressure to achieve this seal. The pressure is only slightly affected when meeting the small area of groove 10 exposed. As the cap 15 moves forward it leaves the primary contact area and moves on and so is only in contact with a small area of change of resistance. This gives a smoother feel to the injection which is very much an advantage for the invention. The proximal groove 11 is similar to the distal groove 10.

Figure 17:
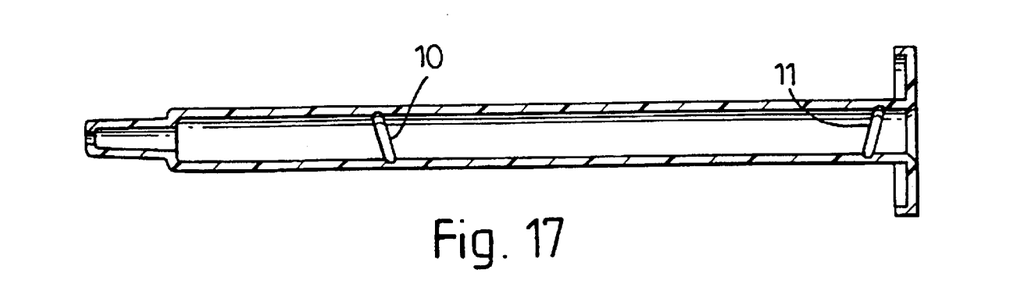
FIG. 17 is a longitudinal section of the barrel which shows the arrangement of grooves in accordance with another embodiment of the invention.

The grooves 10, 11 are very precise in cross-section and are very easy to manufacture in this arrangement. This is an advance from previous inventions, as theoretically it is very difficult to make such a groove in a barrel of one piece. A groove provides a much more solid form of a restrictive means compared to say a projection means. The advantage for moulding grooves 10, 11 is their angle to the longitudinal axis and the axis of withdrawal by the moulding core. This means the projection from the core which forms the groove is able to pass out of the moulded barrel without disturbing the soft inner wall of the barrel. As shown in FIG. 17, the proximal groove 11 can be oriented 180° in axial rotation to the distal groove. This offers less resistance to the moulding core upon withdrawal as the distal projection upon it does not fully locate into the proximal groove 11.

Figure 10:
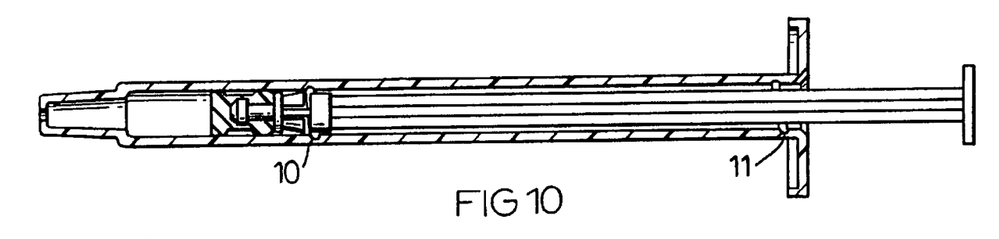
FIGS. 10 to 13 are cross-sectional side elevations of the syringe showing the plunger in different positions.
Figure 11:
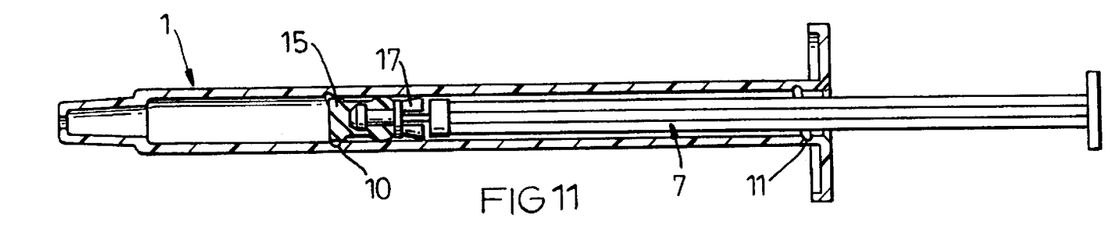

The operation of the syringe is shown in FIGS. 10 to 13. The syringe allows for "normal" use. FIG. 10 shows the plunger in the position it is supplied in. If the plunger was inserted any further it would be rendered unusable due to the flukes 17 passing to the distal side of the groove 10. There are many additions that can be applied to the product which can prevent premature insertion of the plunger but these are not the subject of this invention. The user fills the syringe by pulling back the plunger as in FIG. 11 and is at liberty to fill the syringe to the required level without restrictions. Sometimes a second fill is desired for instance when mixing two liquids in the barrel and this is unhindered. A drug abuser for example will after filling the syringe insert the needle under the skin in an effort to locate a vein suitable for injecting. This action requires retracting the plunger and drawing body fluid into the distal end of the syringe barrel. The colour and quantity of this fluid indicates to the user the suitability of the site. This technique and other are accommodated within the limits of the syringe.

Figure 12:
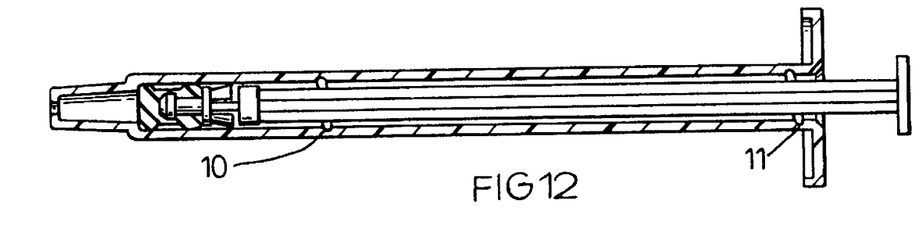

After the injection stroke the plunger will be in a position as shown in FIG. 12. Then if it is required the plunger can be withdrawn a predetermined distance to accommodate aspiration of flushing as it is commonly known, but not further than the groove 10.

Figure 13:
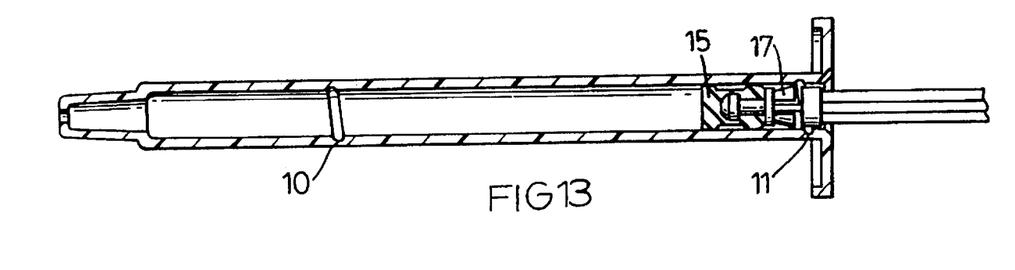

FIG. 13 shows the plunger in the position of maximum withdrawal. At this location the flukes will start to engage with the groove 11, which as described above prevents removal of the plunger and any subsequent tampering that could follow.

Figure 14:
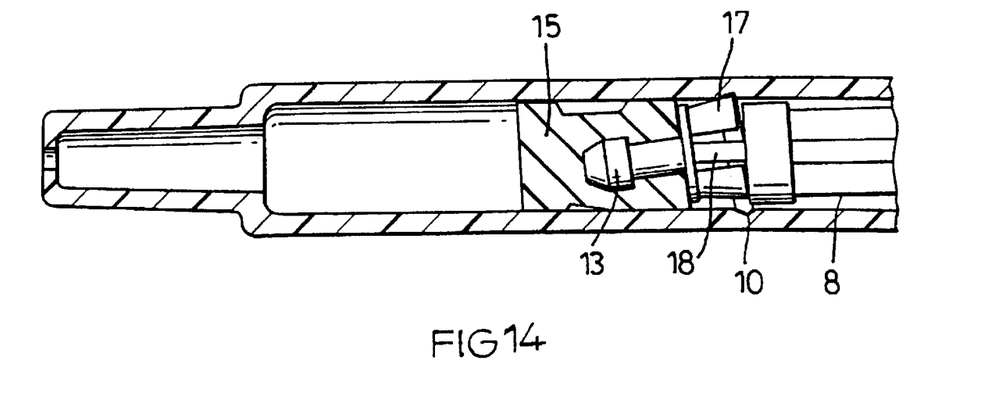
FIG. 14 is a longitudinal section of the distal end region of the syringe, to an enlarged scale, showing the plunger jammed into the groove in the barrel, this being the unusable state.

When the flukes 17 engage with either groove (10 or 11) it results in an engagement shown clearly in FIG. 14. Once the flukes 17 engage with the groove they expand widthways to fill the available space due to the tension moulded into them. This prevents any further rearward movement. The head of the plunger aligns with the angle of the groove as shown and further distorts the normal alignment and so further prevents rearward movement. Furthermore the connection rod 18 touches the rear section of the proximal fluke and so displaces the fluke more outwards and more securely into the groove. The action of the flukes as described acts as a self tightening lock in that the harder the user pulls the plunger in a desire to reuse the syringe the harder it locks itself. If sufficient force is applied the plunger 7 will break at the connection rod 18.

FIG. 15 shows a modification in which the interruption means comprises a projection 29 rather than a groove. The projection 29 is formed as an annulus which is angled to the axis of the barrel 1. The projection 29 is of triangular cross-section. It has a first proximal edge 29' inclined slightly to the inner wall by between 20° and 30°, to allow forward movement of the plunger. The projection 29 also has a second, distal edge 29", sharply inclined to the inner wall, by about 60° to 70°, to engage the locking means on withdrawal. In use, the projection 29 operates in a similar way to the grooves 10, 11. The flukes 17 pass over the projection 29 on forward movement of the plunger 7, but engage with it on withdrawal movement. The engagement twists the head of the plunger, so that it cannot withdraw further.

In a further modification (not shown) the interruption means comprises a groove 10 followed immediately on its proximal side by a projection 29. This provides very satisfactory operation of the locking means 17.

FIGS. 18 to 21 show a modified locking means. Corresponding reference numerals have been applied to corresponding parts. Instead of the flukes 17, the locking means comprises a flexible cross-shaped disc 20. The disc 20 is connected to the base 16 by a short central connector 21, and the connection 18 is also shortened, and connects the disc 20 to the plunger rod 8. The disc 20 has a tapered periphery 22, which is smaller adjacent the base 16. This arrangement reduces the space taken up by the locking means.

Figure 18:
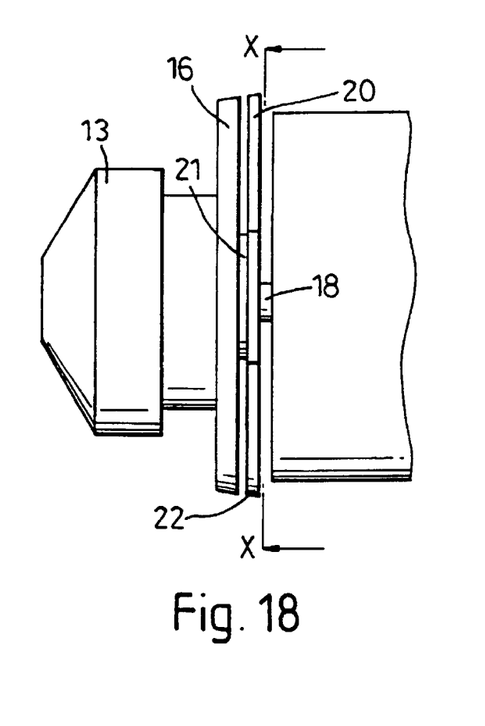
FIG. 18 is a side view of a plunger head with a modified locking means.
Figure 19:
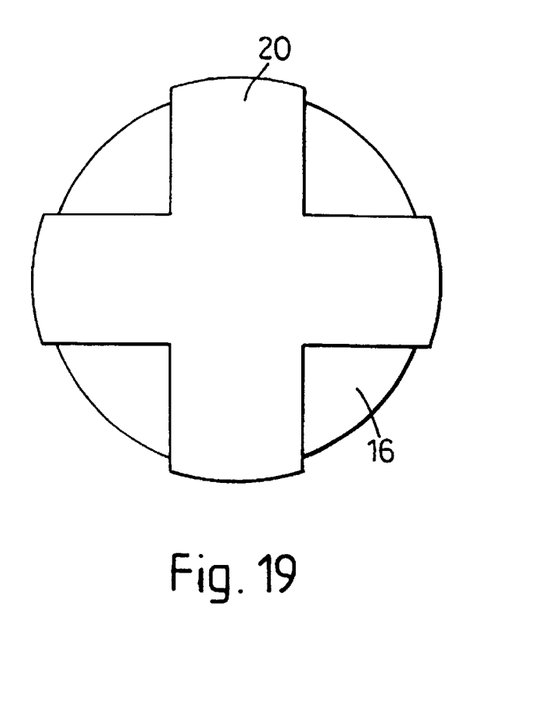
FIG. 19 is a cross-section on the lines X—X of FIG. 18.
Figure 20:
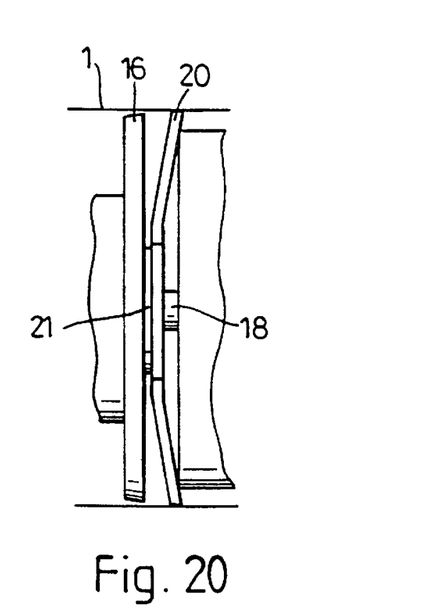
FIG. 20 shows the locking means in the forward movement position.

FIG. 18 shows the plunger 7 at rest, while FIG. 20 shows the plunger moving forwardly. The periphery of the disc 20 deflects away from the base 16, and the side remote from the base 16 engages the plunger rod 8. The disc 20 is therefore supported, and the tapered periphery 22 becomes substantially parallel to the barrel surface (not shown) so that the plunger 7 slides easily, and passes over the groove 10.

Figure 21:
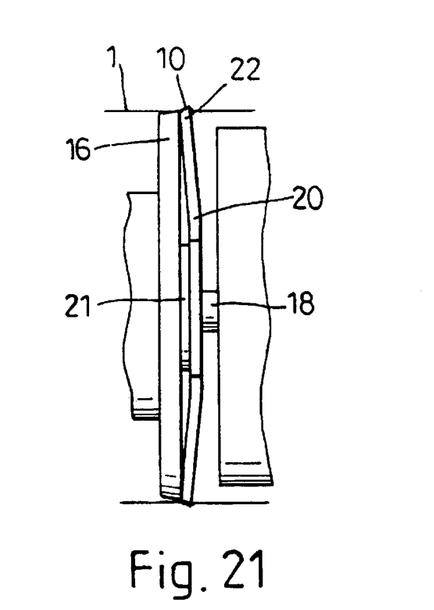
FIG. 21 shows the locking means in the locked position.

On rearward or withdrawal movement the periphery of the disc 20 deflects the other way, and engages with the base 16. In this position it can still slide in the barrel 1, but on reaching a groove 10, 11 the outer edge of the tapered periphery 22 enters the groove and forms a shoulder preventing withdrawal movement out of the groove. As the disc 20 is supported on the base 16 the disc 20 cannot deflect further to slide past the groove 10.

If sufficient force is applied in the locked position, the connection 18 breaks. It may also tend to break inadvertently if the plunger 7 is twisted in normal use. In a modification (not shown), the connection 18 is made larger and the connector 21 smaller in diameter. The connection 18 will then resist the tendency to break on twisting the plunger 7 in normal use. In the locked position, when sufficient force is applied to the plunger 7 the deflected disc 20 acts as a lever on the base 16, so that the connector 21 breaks and the head of the plunger 7 "pops" off.

The modified locking means are shown engaging with a groove 10 which is at right angles to the barrel axis. It would operate just as well with an angled groove, or with the angled projection 29 of FIG. 15.

The barrel 1 and plunger 7 are made of plastics material, by injection moulding. It will be appreciated that each is a single moulding, thus keeping down the cost of manufacture. In fact, the moulding tools for manufacture of existing plungers (those without the locking means) may be modified to include the locking means.

Figure 22:
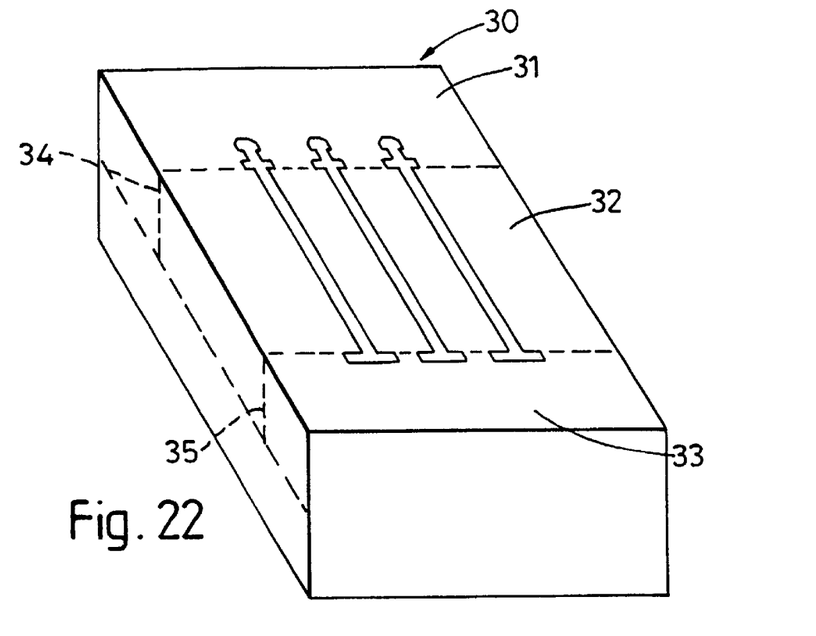
FIG. 22 shows a part of a moulding tool for forming an existing plunger.
Figure 23:
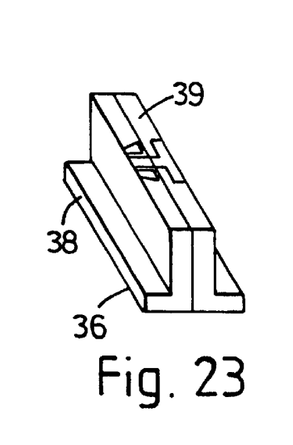
FIG. 23 shows an insert plate for the tool part of FIG. 22.
Figure 24:
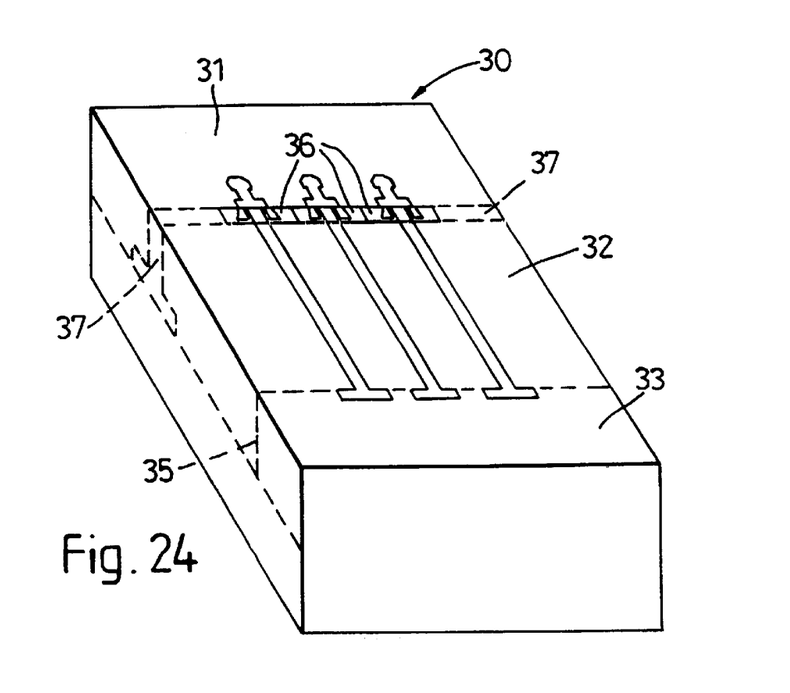
FIG. 24 shows the tool of FIG. 22 modified by the plate of FIG. 23.

FIG. 22 shows one part 30 of a two-part moulding tool for a conventional plunger modified to include the locking means. The tool part 30 contains three impressions of half a plunger; a complementary tool part for containing the impressions of the other half of the plunger is not shown. As can be seen, the tool part is split into three portions 31, 32, 33 with the split lines 34, 35 adjacent the head and gripping flange respectively. In order to modify the tool part 30 for the locking means, inserts 36 containing the impression of half of the locking means are inserted into the part 30 at the split line 34. An insert 36 is shown in FIG. 23; the three inserts 36 inserted into the tool part 30 are shown in FIG. 24. The inserts are held in by packing 37.

The inserts 36 are detachable so that they can easily be changed when they become worn. Wear to the insert containing the locking means is more critical than to the rest of the tool part, since it is essential to the invention that the locking means operates correctly. The inserts can therefore changed, while the rest of the tool is still satisfactory, thus prolonging the life of the tool as a whole.

The insert shown in FIG. 23 has two plates 38, 39. In a modification (not shown) it could have one part, or more than two parts.

In a further modification (not shown) each insert plate 36 may be mounted in the tool part 30 not by packing, but by pins inserted into openings in the tool part 30 and the plate 36.

Furthermore, if the tool part 30 has no existing split lines which can be used, the part 30 may be split to accommodate the inserts 36, or have cavities machined in it to receive them.

What is claimed is:

1. A syringe comprising a barrel and a plunger in slidable and sealing engagement therein, wherein said barrel has a cylindrical surface inner wall, and at least one interruption means interrupting said cylindrical surface, and said plunger has a head, and a locking device, said head carrying a seal and said locking device being adjacent said head and separate from said seal, said locking device operating on engagement with said interruption means on withdrawal of said plunger from said barrel to prevent a further withdrawal movement of said plunger, said barrel being formed as a one-piece moulding and said plunger with said locking device also being formed as a one-piece moulding.

2. A syringe according to claim 1, wherein one said interruption means is arranged adjacent the distal end of said barrel.

3. A syringe according to claim 1, wherein one said interruption means is arranged at the proximal end of said barrel.

4. A syringe according to claim 1, wherein at least one said interruption means is arranged at an angle other than 90° to the longitudinal axis of said barrel.

5. A syringe according to claim 1, wherein at least one said interruption means extends round the whole circumference of said barrel.

6. A syringe according to claim 1, wherein at least one said interruption means is of substantially triangular cross-section.

7. A syringe according to claim 1, wherein at least one said interruption means comprises a projection.

8. A syringe according to claim 1, wherein at least one said interruption means comprises a groove.

9. A syringe according to claim 1, wherein at least one said interruption means comprises a groove followed by a projection.

10. A syringe according to claim 1, wherein said seal of said plunger comprises an elastomeric sealing cap, and said head of said plunger has means with which said elastomeric sealing cap engages, and said locking device is provided on said head of said plunger, adjacent said sealing cap.

11. A syringe according to claim 1, wherein said locking device is so constructed and arranged that, following engagement of said locking device with said interruption means, the locking force increases as the withdrawal force applied to said plunger increases.

12. A syringe according to claim 1, wherein said seal of said plunger comprises an elastomeric sealing cap, and said head of said plunger has means with which said elastomeric sealing cap engages, and said locking device is provided on said head of said plunger, adjacent said sealing cap.

13. A syringe according to claim 12, wherein said locking device comprises a disc attached to said head, said disc having a flexible periphery which slides in each direction, but engages with said interruption means on said withdrawal movement.

14. A syringe according to claim 13, wherein said disc is held by said head in a locked position.

15. A syringe according to claim 13, wherein said disc is cross-shaped.

16. A syringe according to claim 1, wherein said locking device is so constructed and arranged so that, following said engagement of said locking device with said interruption means, the locking force increases as the withdrawal force applied to said plunger increases.

17. A syringe comprising a barrel and a plunger in slidable and sealing engagement therein, wherein said barrel has a cylindrical surface inner wall, and at least one interruption means interrupting said cylindrical surface, and said plunger has a head and a locking means, said head carrying a seal, and said locking means being adjacent said head, said locking means operating on engagement with an interruption means on withdrawal of said plunger to prevent a further withdrawal movement, and wherein at least one said interruption means is at an angle other than 90° to the longitudinal axis of said barrel.

18. A syringe according to claim 17, wherein at least one said interruption means extends round the whole circumference of said barrel.

19. A syringe according to claim 17, wherein at least one said interruption means is of substantially triangular cross-section.

20. A syringe according to claim 17, wherein at least one said interruption means comprises a projection.

21. A syringe according to claim 17, wherein one said interruption means is arranged adjacent the distal end of said barrel.

22. A syringe according to claim 17, wherein one said interruption means is arranged at the proximal end of said barrel.

23. A syringe comprising a barrel and a plunger in slidable and sealing engagement therein, wherein said barrel has a cylindrical surface inner wall, at least one interruption means interrupting said cylindrical surface, and said plunger has a head and a locking means, said head carrying a seal, and said locking means being adjacent said head, said locking means operating on engagement with an interruption means on withdrawal of said plunger to prevent a further withdrawal movement, and wherein at least one said interruption means comprises a groove.

24. A syringe comprising a barrel and a plunger in slidable and sealing engagement therein, wherein said barrel has a cylindrical surface inner wall, and at least one interruption means interrupting said cylindrical surface, and said plunger has a head and a locking means, said head carrying a seal, and said locking means being adjacent said head, said locking means operating on engagement with an interruption means on withdrawal of said plunger to prevent a further withdrawal movement, and wherein at least one said interruption means comprises a groove followed by a projection.

25. A syringe comprising a barrel and a plunger in slidable and sealing engagement therein, wherein said barrel has a cylindrical surface inner wall, and at least one interruption means interrupting said cylindrical surface, and said plunger has a head and a locking means, said head carrying a seal, and said locking means being adjacent said head, said locking means operating on engagement with an interruption means on withdrawal of said plunger to prevent a further withdrawal movement, and wherein said seal of said plunger comprises an elastomeric sealing cap, said head of said plunger having means with which said elastomeric sealing cap engages, with said locking means being provided on said head of said plunger adjacent said sealing cap, and said locking means comprises a disc attached to said head, said disc having a flexible periphery which slides in each direction, but engages with said interruption means on said withdrawal movement.

26. A syringe according to claim 25, wherein said disc is held by said head in a locked position.

27. A syringe according to claim 25, wherein said disc is cross-shaped.

* * * * *

UNITED STATES PATENT AND TRADEMARK OFFICE
CERTIFICATE OF CORRECTION

PATENT NO. : 6,368,306 B1
DATED : April 9, 2002
INVENTOR(S) : Koska

It is certified that error appears in the above-identified patent and that said Letters Patent is hereby corrected as shown below:

<u>Title page,</u>
Item [73], Assignee, insert -- Star Syringe Limited --

Signed and Sealed this

Eleventh Day of November, 2003

JAMES E. ROGAN
*Director of the United States Patent and Trademark Office*